United States Patent [19]

Nakajo et al.

[11] Patent Number: 5,920,387

[45] Date of Patent: Jul. 6, 1999

[54] APPARATUS AND METHOD FOR SURFACE INSPECTION

[75] Inventors: Masahiro Nakajo, Hirakata; Ken Tatsuta, Kadoma, both of Japan

[73] Assignee: Matsushita Electric Industrial Co., Ltd., Osaka-fu, Japan

[21] Appl. No.: 09/023,565

[22] Filed: Feb. 13, 1998

[30] Foreign Application Priority Data

Feb. 18, 1997 [JP] Japan .................................. 9-033506

[51] Int. Cl.⁶ .................................................. G01N 21/00
[52] U.S. Cl. ..................... 356/237.4; 356/237.5; 356/237.3
[58] Field of Search ............... 356/237.1–237.5

[56] References Cited

U.S. PATENT DOCUMENTS

| | | |
|---|---|---|
| 4,740,708 | 4/1988 | Batchelder ........................ 356/237.3 |
| 4,831,274 | 5/1989 | Kohno et al. . | |

FOREIGN PATENT DOCUMENTS

| | | |
|---|---|---|
| 6-258235 | 9/1994 | Japan . |
| 7-159336 | 6/1995 | Japan . |

OTHER PUBLICATIONS

"Laser Range Finder Based on Synchronized Scanners," Marc Rioux, vol. 23, No. 21, pp. 3837–3844, issued Nov. 1, 1984.

*Primary Examiner*—Robert Kim
*Assistant Examiner*—Amanda Merlino
*Attorney, Agent, or Firm*—Wenderoth, Lind & Ponack, L.L.P.

[57] ABSTRACT

An optical element is provided, to move an optical axis of a scanning light incident to a substrate so that illumination positions on photodetecting faces of two photodetectors agree or almost agree with each other. Respective surface information signals sent out from the two photodetectors are accordingly agreed or a difference of the signals is minimized, whereby the measuring accuracy in surface inspection is improved.

6 Claims, 8 Drawing Sheets

APPARATUS AND METHOD FOR SURFACE INSPECTION

BACKGROUND OF THE INVENTION

The present invention relates to an apparatus and a method for inspecting a surface state of an object to be inspected through scanning. Specifically, the present invention relates to an apparatus and a method for inspecting surface states of substrates with components mounted, liquid crystal panel elements, semiconductor wafers, electronic components, etc., by scanning light onto the surfaces. More particularly, the present invention relates to an apparatus and a method of inspecting for positional shifts of the mounted components, missing components, soldering failures, levitation of components before being soldered, shape failures of components, etc.

As a way to inspect a surface state of substrates having components mounted thereon, recently, a surface inspection apparatus using a scanning of a laser light has often been used, which is constituted to often been often used. This apparatus is arranged as shown in FIG. 8. A laser light emitted from a semiconductor laser diode 1 is turned to a projection beam 3 through a collimator lens 2. The projection beam 3 is brought onto a polygon mirror 4 of a polygonal section rotating about a center shaft 10 in a circumferential direction. Each peripheral face of the polygon mirror 4 is a mirror face 4a parallel to an axial direction of the center shaft 10. The laser beam is reflected at the mirror face 4a and becomes a reflected light 5. The projection beam 3 strikes the mirror face 4a from a direction orthogonal to the axial direction of the center shaft 10. Since the polygon mirror 4 rotates in a direction of an arrow about the center shaft 10 while receiving the projection beam 3 at the mirror face 4a, the reflected light 5 is deflected to one direction indicated by an arrow I of FIG. 3. The deflected reflected light 5 enters an fθ lens system 6 comprising a plurality of coaxially arranged lenses, is deflected and condensed by the system 6, and forms an image at a surface 7a of a substrate 7 to be inspected. A scanning light thus focused on the surface 7a scans the surface 7a in accordance with the rotation of the polygon mirror 4. A resulting scattered reflected light 8 at the surface 7a of the substrate 7 is, as shown in FIG. 9, which is a side view of FIG. 8) sent by a lens 11 to respective photodetecting faces of two photodetectors 9 separated 180° via an optical axis of the scanning light. That is, the photodetectors are disposed symmetrically to each other in relation to the optical axis. The photodetector 9 photoelectrically converts the scattered reflected light 8 collected on to the photodetecting face thereof and sends out electric signals corresponding to a position of the scattered reflected light on the photodetecting face to an arithmetic device 13. The arithmetic device 13 determines a height of an object 12 to be measured on the surface 7a based on the electric signals supplied from the photodetectors 9 according to a known triangulation method.

As shown in FIG. 9, the photodetectors 9 are oriented in two directions. Thus, even if one scattered reflected light 8 is blocked by a step difference formed by the objects 12 to be measured which are mounted on the substrate 7 and therefore cannot reach one of the photodetectors, the other scattered reflected light 8 can reach the other photodetector 9. So, the other photodetector 9 is utilized to detect the other scattered reflected light.

In the case of the conventional surface inspection apparatus 20 arranged as above, while the surface state of the substrate 7 or the like can be inspected photoelectrically, it may happen that the illumination position on the photodetecting face of one photodetector 9 disagrees with the illumination position the other photodetector 9. This may happen because of the photodetectors are arranged in two directions. Thus a difference is caused between each of the signals output from the respective photodetectors 9 resulting in a measuring error. Particularly, if the reflected light 8 is blocked as discussed above and the photodetector 9 is switched to another one, the measuring error becomes large.

SUMMARY OF THE INVENTION

The present invention has been devised to solve the above disadvantage inherent in the conventional art. Its object is to provide an apparatus and a method for surface inspection whereby the measuring accuracy in surface inspection is improved.

A surface inspection apparatus according to a first aspect of the present invention compromise a laser element for emitting a laser light; and a deflecting scanning mirror having a polygonal periphery. Each peripheral face of the periphery is a mirror face, and the deflecting scanning mirror rotates about a center shaft thereof in a peripheral direction for reflecting the laser light emitted from the laser element during the rotation around the center shaft. The laser light strikes the mirror face from a direction orthogonal to an axial direction of the center shafts.

Two photodetectors are provided each for detecting a scattered reflected light at a surface of an object to be inspected when a reflected laser light, reflected by the deflecting scanning mirror, scans the surface of the object. The photodetectors and which are arranged symmetrically with respect to an optical axis of the scanning light. The surface of the object is inspected based on illumination positions at photodetecting faces of the photodetectors.

An optical element is disposed between the deflecting reflected mirror and the object for moving an optical axis of the reflecting light reflected by the deflecting scanning mirror. This makes the illumination positions at photodetecting faces of the respective photodetectors agree or nearly agree with each other, thus minimizing a surface inspection error.

A surface inspection method according to a second aspect of the present invention comprises a surface inspection method which comprises:

emitting a laser light to a deflecting scanning mirror having a polygonal periphery. Each peripheral face of the periphery is a mirror face, and the deflecting scanning mirror rotates about a center shaft thereof in a peripheral direction for reflecting the emitted laser light during the rotation around the center shaft. The laser light strikes the mirror face from a direction orthogonal to an axial direction of the center shaft.

A surface of an object to be inspected is scanned by a scanning light which is the reflected light reflected at the mirror faces.

Scattered reflected light reflected at the surface of the object are detected by two photodetectors set symmetrically with respect to an optical axis of the scanning light, thereby inspecting the surface of the object.

When the scanning light is projected, the optical axis of the scanning light to the surface of the object is moved so that illumination positions at photodetecting faces of the respective photodetectors agree or nearly agree with each other thereby to minimize a surface inspection error.

According to the surface inspection apparatus in the first aspect of the present invention and the surface inspection method in the second aspect of the present invention, an optical element is provided which can move the optical axis of the reflecting light reflected by the deflecting mirror. The surface information signals output from two photodetectors can hence agree with each other or a difference of the signals can be made minimized by moving the optical axis of the reflecting light. So, the measuring accuracy in surface inspection is improved.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE PREFERRED EMBODIMENT

Figure 1:
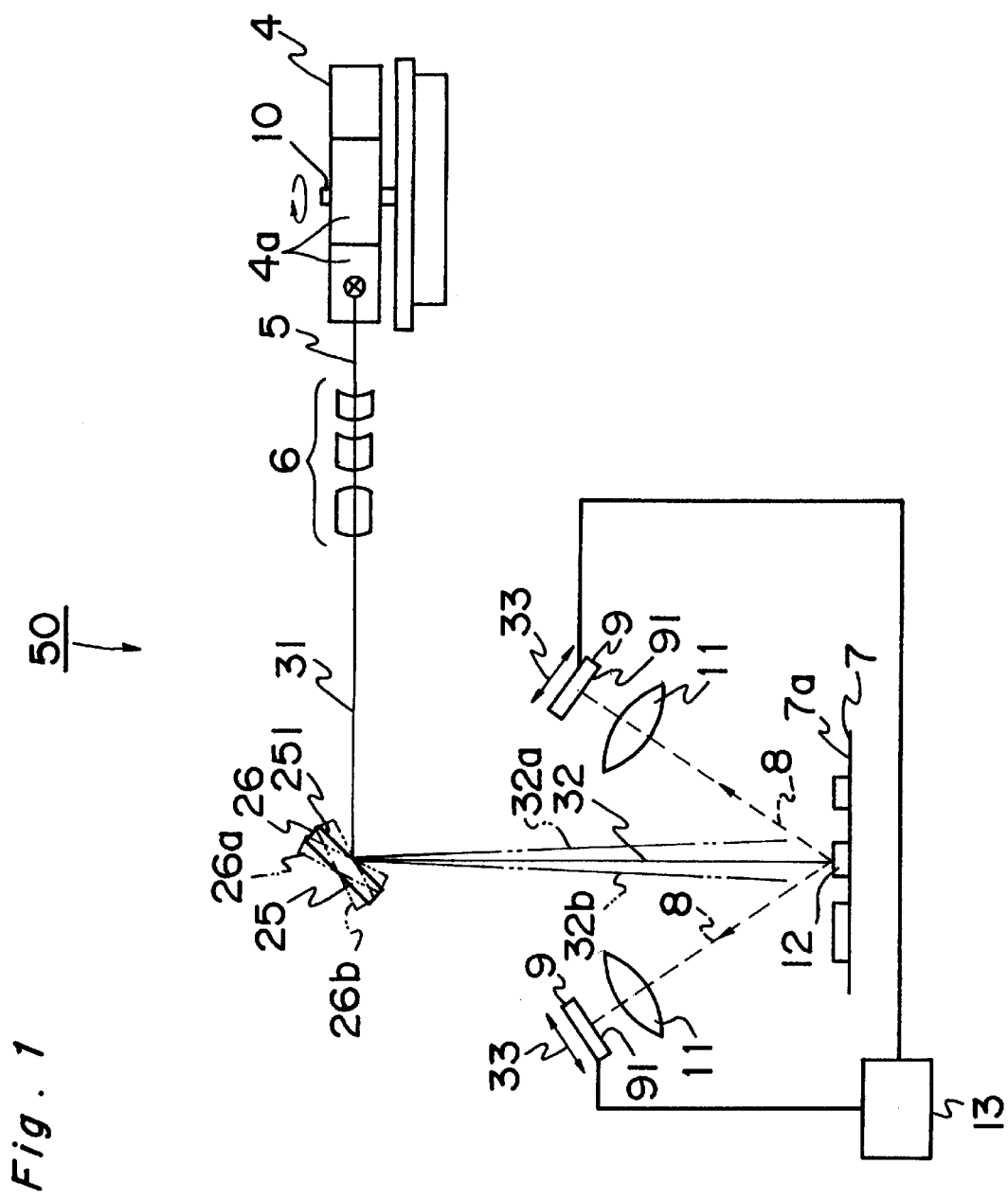
FIG. 1 is a side view showing the arrangement of a surface inspection apparatus according to one embodiment of the present invention.

A surface inspection apparatus and a surface inspection method in a preferred embodiment of the present invention will be described with reference to the drawings. It is to be noted that like parts are designated by like reference numerals throughout the accompanying drawings. The surface inspection method is carried out by the surface inspection apparatus. A polygon mirror 4 embodies a function of the deflecting scanning mirror. Although a substrate having an electronic component mounted thereon is exemplified as an object to be inspected in the present embodiment, the object to be inspected is not limited to this.

Figure 2:
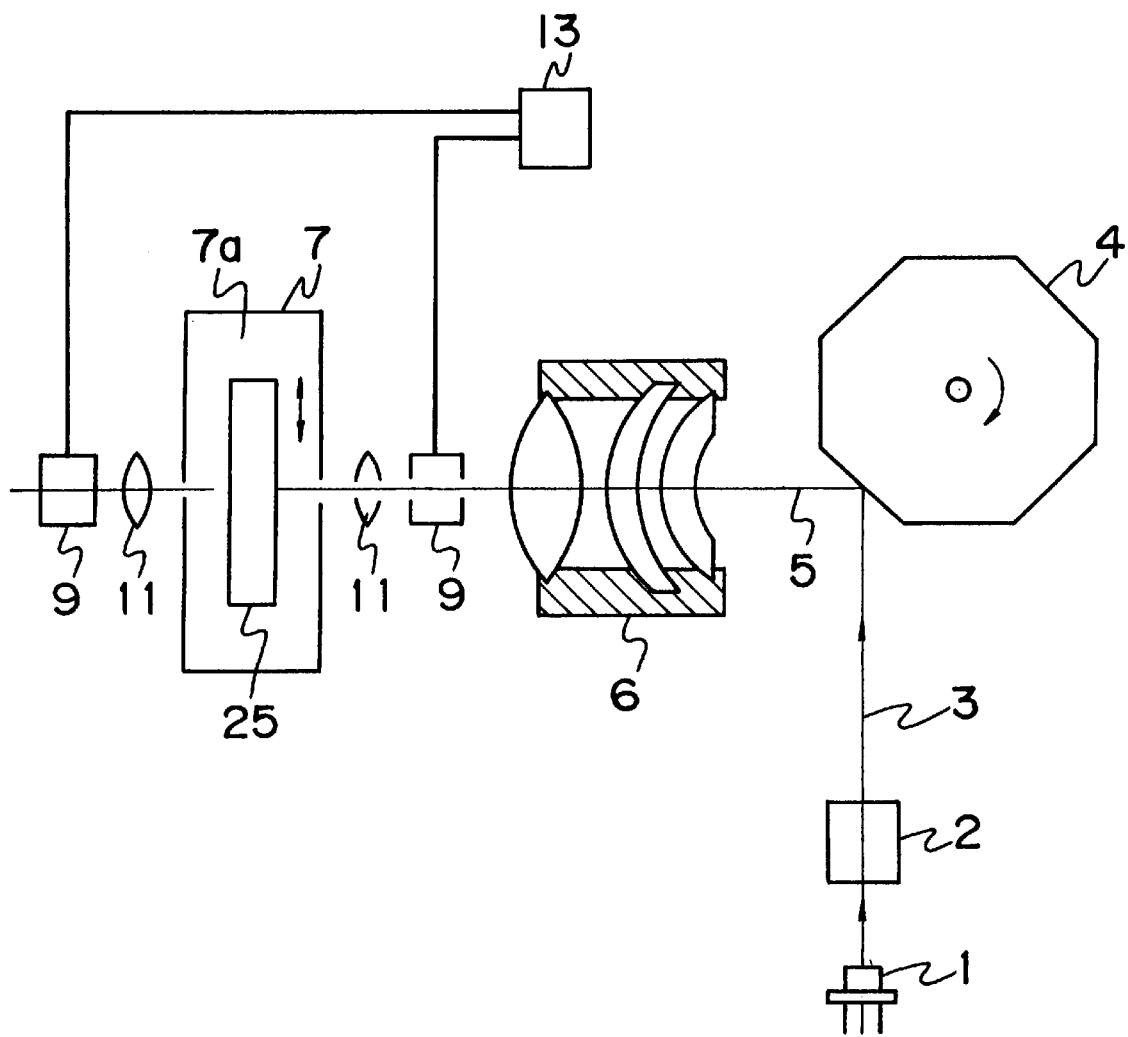
FIG. 2 is a plan view of the surface inspection apparatus of FIG. 1.
Figure 4:
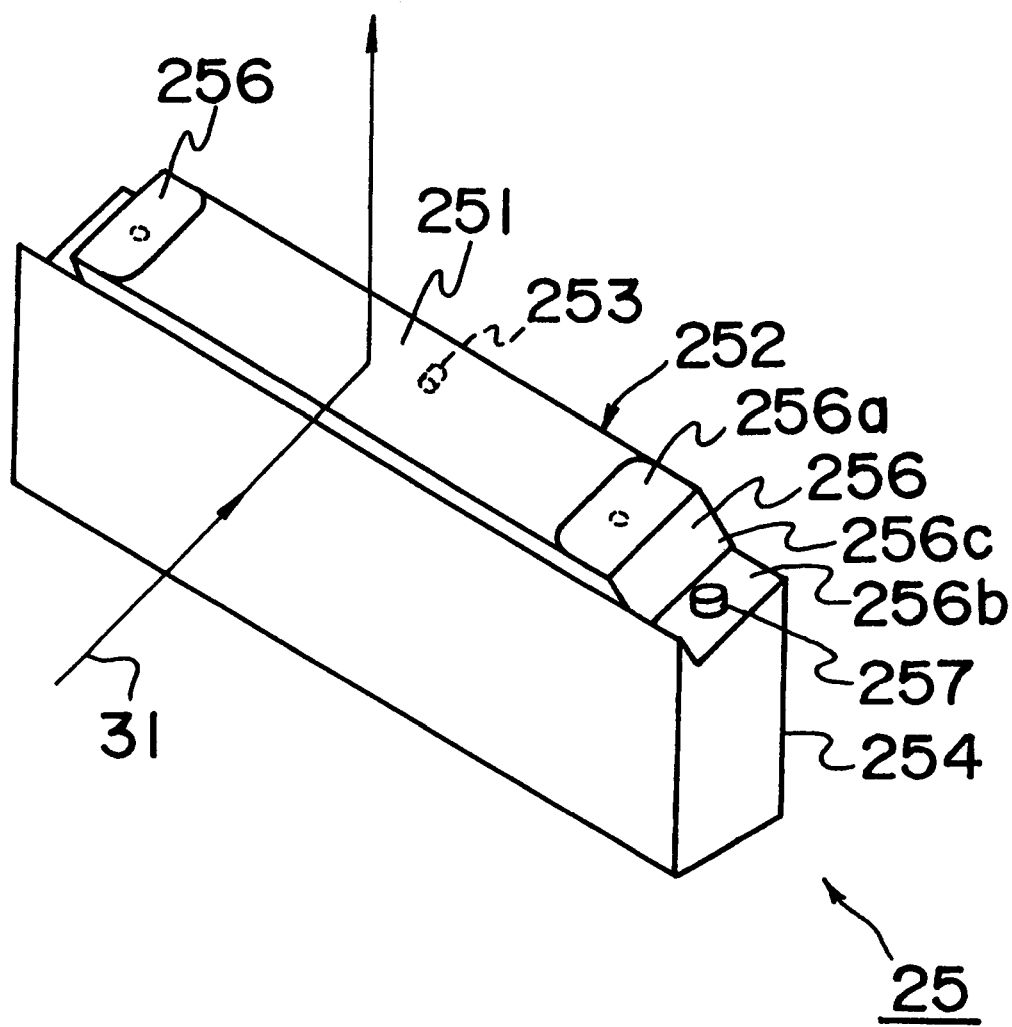
FIG. 4 is a perspective view of an optical element of FIG. 1.
Figure 5:
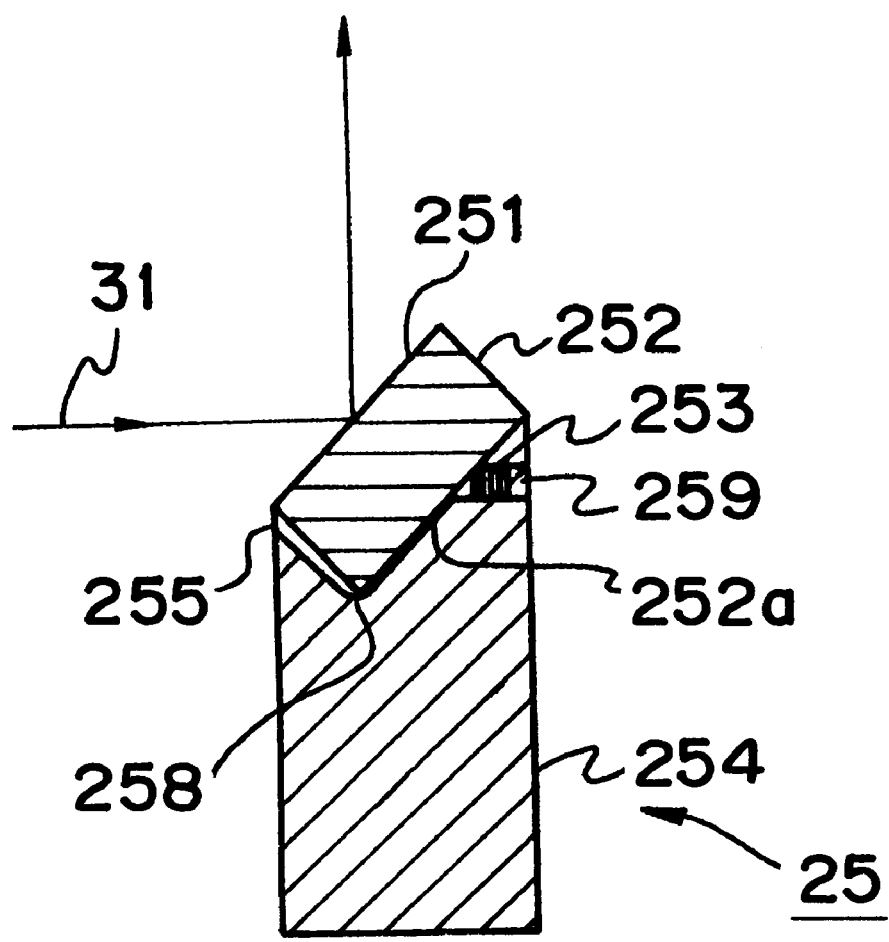
FIG. 5 is a sectional view of the optical element of FIG. 4.

As shown in FIGS. 1 and 2, a surface inspection apparatus 50 according to the embodiment includes a semiconductor laser diode 1, a collimator lens 2, a polygon mirror 4, an fθ lens system 6, two photodetectors 9 and lenses 11, similar to the conventional surface inspection apparatus 20. These parts comprising the apparatus are the same as those of the surface inspection apparatus 20, and therefore the description thereof will be omitted here. The surface inspection apparatus 50 is different from the surface inspection apparatus 20 in that an optical element 25 is provided between the fθ lens system 6 and the substrate 7 so as to reflect a reflected light 31 projected from the fθ lens system 6 as a scanning light 32 towards a surface 7a of the substrate 7. The optical element 25 moves an optical axis of the scanning light 32 by changing an inclining angle of a reflection face of the element 25. The movement of the optical axis makes surface information signals output from the two photodetectors 9 agree with each other or minimizing a difference of the signals. The optical element 25 is constructed as shown in FIGS. 4 and 5.

More specifically, the optical element 25 comprises a reflecting body 252 having the reflection face 251 and a reflection angle-changing member 253 for changing the inclining angle of the reflection face 251. The reflecting body 252 is formed of strip-shaped glass having a breadth of approximately 10–20 mm and a length of approximately 50–60 mm. The reflection face 251 is a mirror face. The reflecting body 252 is pressed at both end parts of a longitudinal direction thereof by retainer members 256 and accordingly held at a V-shaped notch 255 formed in a pedestal 254. Each of the retainer members 256 has a pressing part 256a, a fixed part 256b and a coupling part 256c coupling an end part of the pressing part 256a and that of fixed part 256b. The pressing part 256a and fixed part 256b each formed of a thin metallic plate extend parallel to each other in the same direction with a step difference. The pressing part 256a, fixed part 256b and coupling part 256c are integrated into the retainer member 256 of one body. In such retainer members 256, each fixed part 256b is fitted at the notch 255 by a mounting screw 257 with the reflecting body 252 being held between the pressing part 256a and the notch 255. At this time, the longitudinal direction of the reflecting body 252 is in alignment with the direction from the pressing part 256a to the fixed part 256b. The retainer members 256 elastically press both end parts in the longitudinal direction of the reflecting body 252 at a fulcrum of the mounting screws 257 to the pedestal 254. The reflecting body 252 is thus supported by the pedestal 254. Owing to this arrangement, the reflecting body 252 can swing so that the inclining angle of the reflection face 251 is changeable by the reflection angle-changing member 253 as will be described later. The notch 255 is formed in such a shape as to allow the reflecting body 252 to swing.

Figure 7:
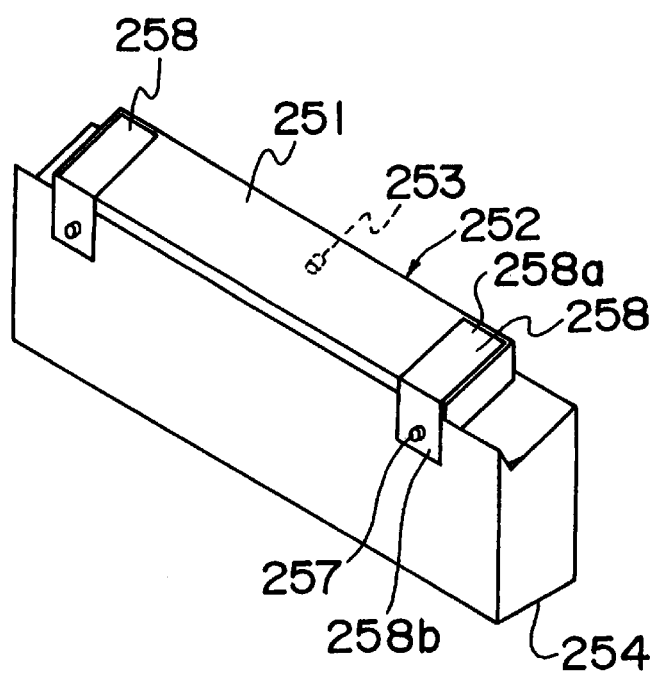
FIG. 7 is a perspective view showing a different state of a retainer member mounted for pressing a reflecting body of the optical element of FIG. 1 to a pedestal.
Figure 8:
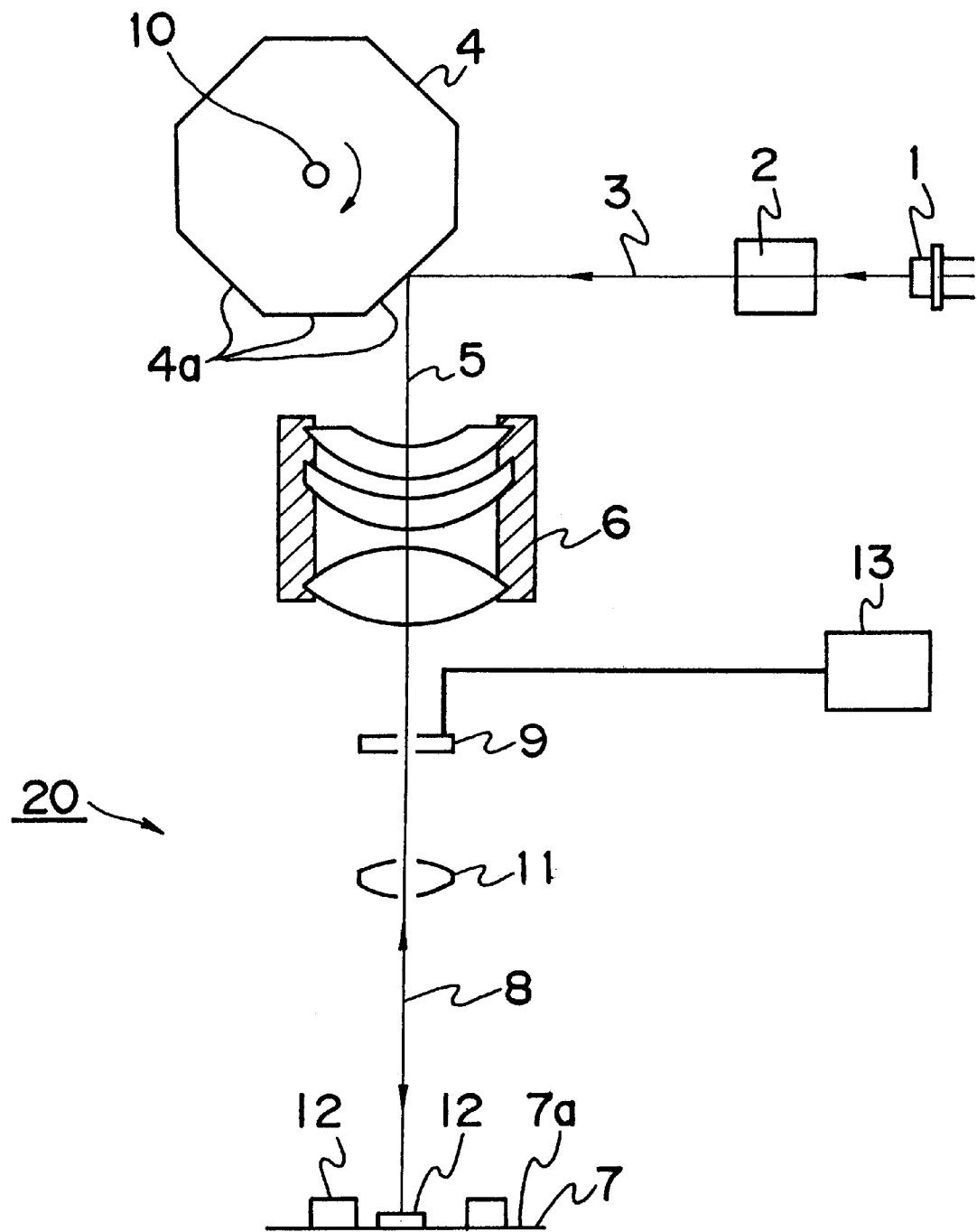
FIG. 8 is a diagram showing the arrangement of a conventional surface inspection apparatus.
Figure 9:
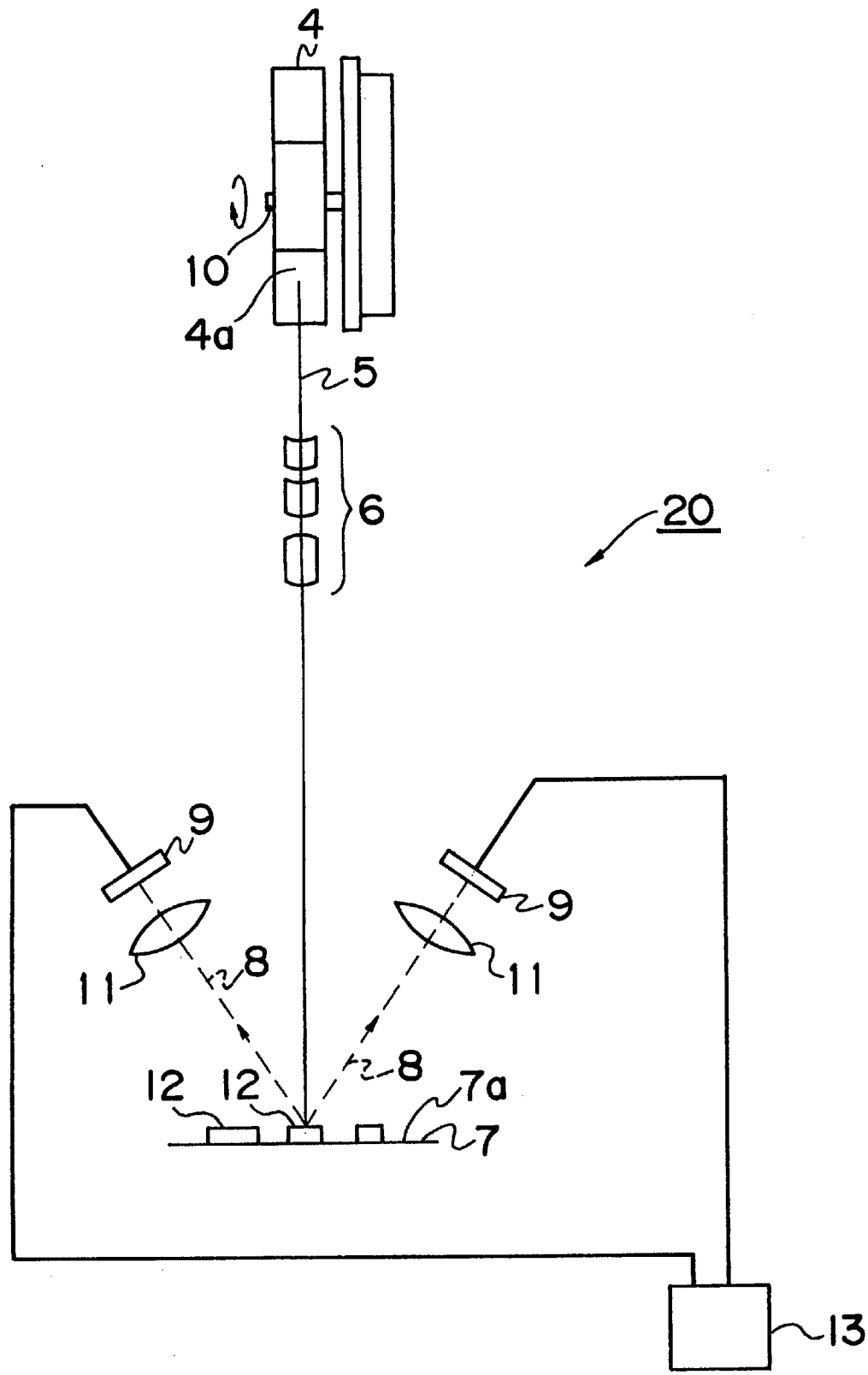
FIG. 9 is a side view of the surface inspection apparatus of FIG. 8.

How to fit the retainer member 256 to the reflecting body 252 is not restricted to the foregoing manner. For instance, as indicated in FIG. 7, a retainer member 258 can be mounted to the pedestal 254 so that a pressing part 258a is directed to a fixed part 258b of the retainer member 258 in a direction orthogonal to the longitudinal direction of the reflecting body 252. However, in the example of FIG. 7, since the longitudinal direction of the reflecting body 252 is not alignment with the direction from the pressing part 258a to the fixed part 258b, a difference of thermal expansion coefficients of the glass reflecting body 252 and metallic retainer member 258 causes a difference in the amount of expansion between the reflecting body 252 and retainer member 258 when an the ambient temperature is increased. As a result, the inclining angle of the reflection face 251 is possibly changed. On the other hand, when the pressing part 256a and fixed part 256b are aligned in the same direction as the longitudinal direction of the reflecting body 252 as in FIG. 4, the aforementioned disadvantage is eliminated, and therefore the embodiment is preferred to the example of FIG. 7.

The reflection angle-changing member 253 is a screw engaged in a penetration hole 259 which is formed in the pedestal 254 and opened at the notch 255. The changing member 253 advances and retreats at an acute angle to a rear face 252a opposed to the reflection face 251 of the reflecting body 252 set at the notch 255. When the changing member 253 advances and retreats against the rear face 252a, the reflecting body 252 at the notch 255 can swing with a minute angle about the fulcrum 257, whereby the inclining angle of the reflection face 251 is changed. According to the present embodiment, although there is provided only one reflection angle-changing member 253 to touch a central part in the longitudinal direction of the reflecting body 252 in order to facilitate the adjustment of the angle of the reflection face 251, the reflecting body 252 can swing uniformly all over the whole reflection face 251.

The above-arranged optical element 25 is installed at the projection side of the fθ lens system 6 as shown in FIGS. 1 and 2. In the optical element 25, the reflected light 31 projecting from the fθ lens system 6 is reflected at the reflection face 251 and cast to the surface 7a of the substrate 7 as the scanning light 32 as shown in FIGS. 4 and 5. The location of the optical element 25 is not limited to that of the embodiment, but can be arranged between the polygon mirror 4 and fθ lens system 6. However, it is not preferable to arrange the optical element 25 between the semiconductor laser diode 1 and polygon mirror 4, because a scanning line of the scanning light 32 on the surface 7a of the substrate 7 would be curved.

The operation at the optical element 25 arranged as above will be described here. When the reflecting body 252 is inclined by the changing member 253 to a swinged position 26a indicated in FIG. 1 from a set position 26 of the reflecting body 252 represented by a solid line in FIG. 1 thereby to change the inclining angle of the reflection face 251, the optical axis of the scanning light 32 in the set position 26 is moved and the light becomes a scanning light 32a. On the other hand, when the inclining angle of the reflection face 251 is changed to a swinged position 26b, the scanning light 32 is turned to a scanning light 32b with the optical axis changed. As the optical axis of the scanning light 32 is moved, the optical axis of the scattered reflected light 8 reflected at the surface 7a of the substrate 7 is moved as well. Consequently the illumination position on the photodetecting face 91 of each photodetector 9 is moved in a direction of an arrow 33. The scattered reflected light 8 from the scanning light 32 corresponding to the set position 26 hits the photodetecting face 91 of each photodetector 9. If the illumination position is different between the two photodetecting faces 91. In other words, different information signals are output from the photodetectors 9), the angle of the reflection face 251 of the reflecting body 252 is changed by the changing member 253 so that the illumination positions to the photodetecting faces of the photodetectors 9 agree or nearly agree with each other. The optical axis of the scanning light 32 is thus moved, so that the optical axis of each scattered reflected light 8 is moved. Through this operation, illumination positions at the photodetecting faces 91 of the two photodetectors 9 are agreed or almost agreed, making the information signals from the two photodetectors 9 agree with each other or assume a minimum difference.

The operation of the surface inspection apparatus 50 in the arrangement of the embodiment will be now described. Since the apparatus 50 operates fundamentally in the same manner as the conventional surface inspection apparatus 20, the description of the basic operation will be omitted.

After the apparatus 50 is tentatively assembled, a flat ceramic plate having a uniform surface state is set as a temporary substrate 7 at a set position of a substrate, and laser beams are projected to the ceramic plate experimentally. Preferably, the apparatus 50 is set such that height information obtained by the experimental projection to the flat ceramic plate is information corresponding to a the middle of an inspection range. The experimental projection is carried out to confirm whether the surface information signals output from the photodetectors 9 agree or a difference of the signals is minimum. Unless the information signals agree or the difference is minimum, the reflection angle-changing member 253 is advanced or retreated. This adjustment will change the inclining angle of the reflection face 251 of the reflecting body 252 and move the optical axis of the scanning light 32, and eventually move the optical axis of each scattered reflected light 8. Accordingly, the illumination positions at the photodetecting faces 91 of the photodetectors 9 are agreed or nearly agreed with each other, and the information signals from the photodetectors 9 are agreed or the difference of the information signals is minimized. The assembly of the surface inspection apparatus 50 is completed at this stage. After the ceramic substrate is removed, the apparatus 50 is used to execute a surface inspection as follows.

Figure 3:
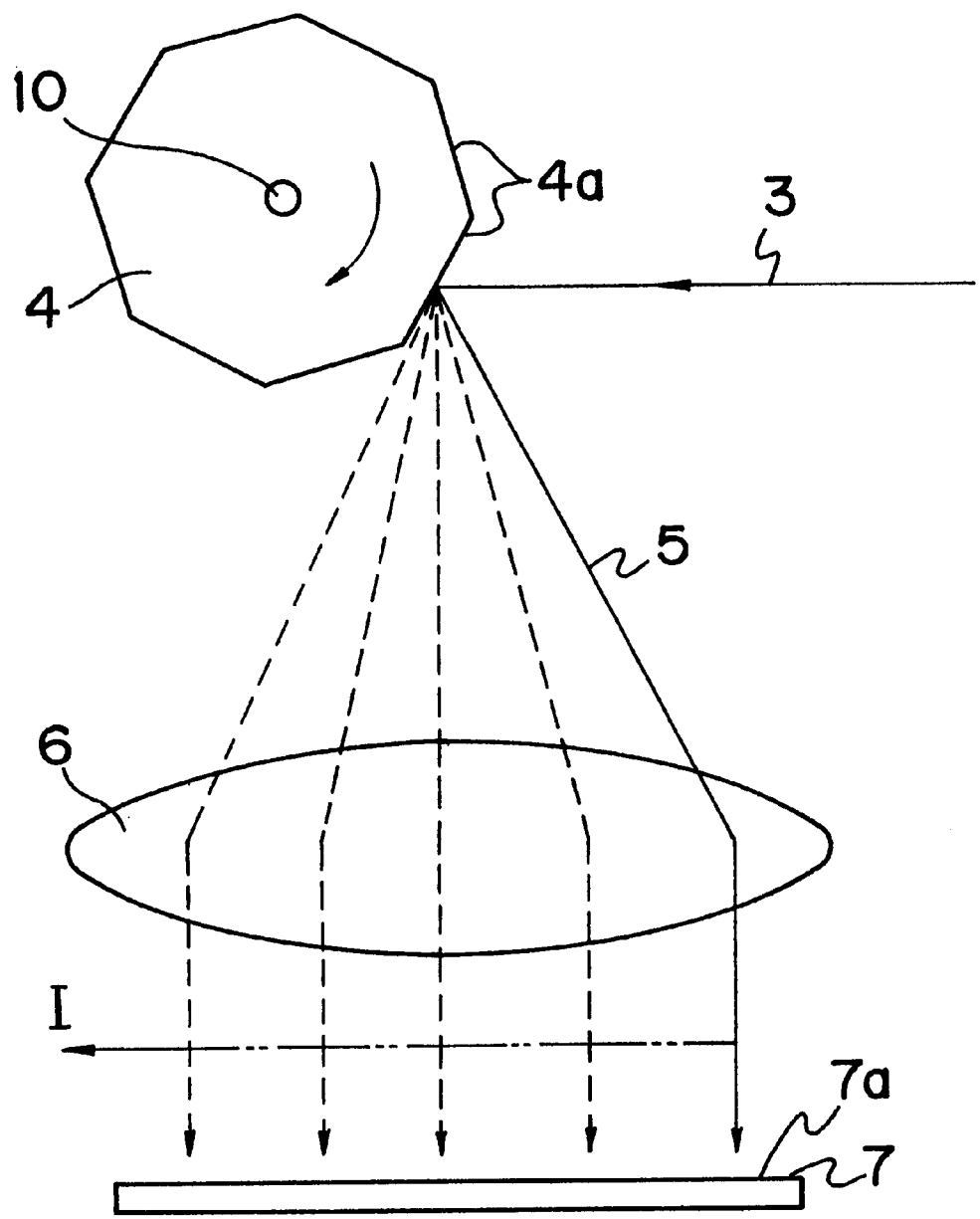
FIG. 3 is a diagram of a rotating direction of a polygon mirror and a scanning direction of light on a substrate in FIG. 1.

The laser light from the semiconductor laser diode 1 becomes the projection beam 3 through the collimator lens 2, hits the mirror face 4a of the polygon mirror 4 and is turned to the reflected light 5. Since the polygon mirror 4 rotates about the center shaft 10, the reflected light 5 is deflected in one direction and enters the fθ lens system 6. The fθ lens system 6 applies the action of a condenser lens to the reflected light 5 as shown in FIG. 3. Although the fθ lens system 6 is shown to have one lens in FIG. 3 for the sake of convenience, the fθ lens system 6 is actually comprised of a plurality of coaxially arranged lenses as in FIG. 2. The reflected light 31 projected from the fθ lens system 6 is reflected to be the scanning light 32 at the optical element 25 having the inclining angle of the reflection face 251 adjusted beforehand as described earlier. The scanning light enters always at right angles to the surface 7a of the substrate 7 and scans the surface 7a. Thus, no blind spot is given rise to the incident scanning light 32 even when the object 12 to be measured is present at the surface 7a of the substrate 7.

The scattered reflected light 8 generated at the surface 7a of the substrate 7 is, via the photodetecting lenses 11, brought onto the photodetecting faces 91 of the photodetectors 9. Each photodetecting lens 11 has an angle of field covering a scanning width to the respective photodetector 9. The lens focuses the respective scattered reflected light 8 so that the illumination position is moved on each photodetecting face 91 of the photodetectors 9 in the arrow direction 33 in accordance with a height of the object 12 to be measured on the substrate 7. In response to the projections on the respective photodetecting faces 91, each photodetector 9 outputs time series surface information signals proportional to the moving amount of the illumination position in the arrow direction 33 synchronously with the scanning of light. The information signals are supplied to the arithmetic device 13, whereby a three-dimensional shape of the object 12 to be measured at the substrate 7 is inspected.

For selecting the signals of the photodetectors 9 at the arithmetic device 13, each threshold level is set for the respective photodetecting light sums of the supplied surface information signals. Which of the signals is to be selected is determined based on whether each photodetecting light sum of the supplied surface information signals is not smaller than the threshold level. If each photodetecting light sum of both photodetectors 9 shows the threshold level or larger, an average value of both surface information signals is used. If both photodetecting light sums are smaller than the threshold level respectively, the inspection is judged as an error.

In the surface inspection apparatus 50 of the present embodiment, the optical element 25 which can minutely adjust the optical axis of the scanning light 32 is provided, so that surface information signals output from two photodetectors 9 can be agreed with each other or a difference of the signals can be made minimum. Accordingly, the inspection accuracy in surface inspection is improved.

It may be conceived to incline the polygon mirror 4 itself by inclining the rotary shaft 10 thereof, in place of using the optical element 25 of the embodiment, so as to move the optical axis of the scanning light 32. In this method, however, the projected beam 3 does not enter the mirror face 4a of the polygon mirror 4 orthogonally to the axial direction of the rotary shaft 10 and the scanning line by the scanning light 32 on the surface 7a of the substrate 7 is undesirably not straight, but curved.

Figure 6:
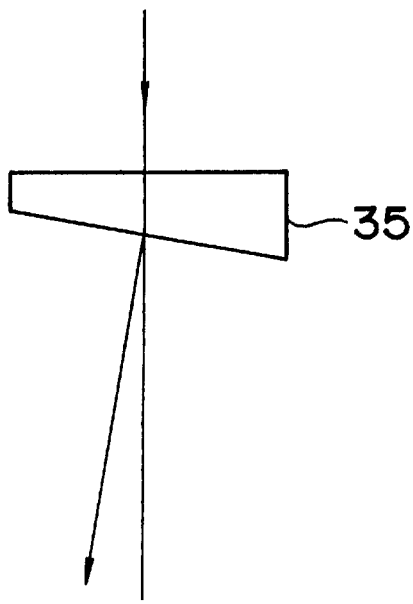
FIG. 6 is a diagram of the optical element of FIG. 1 in a different embodiment.

Other than the reflecting body 252 employed in the embodiment, a wedge-shaped prism 35 as shown in FIG. 6 may be used as the optical element for moving the optical axis of the scanning light 32. Attention should be taken to insert the prism 35 in a luminous flux of parallel beams. If the prism 35 is not inserted into parallel beams, an aberration is generated, which worsens the shape of the spot of the scanning light 32 to the object 12 to be measured.

When a whole surface of the substrate 7 is inspected, this inspection is executed by operating a movement of the substrate 7 and a scanning of light alternatively. In this case, the substrate is moved by a substrate-moving device such as a linear motor or a combination of a motor and a ball screw, etc. at right angles to the scanning direction of light. Needless to say, the inspection apparatus may be moved while the substrate 7 is kept stationary.

According to the above-described embodiment, the object to be inspected is the substrate 7. The surface inspection apparatus and method of the embodiment can be used to inspect surface states of not only the substrate, but circuit boards before components are mounted thereon, electronic components, liquid crystal panels or objects requiring a three-dimensional measurement, etc.

The entire disclosure of Japanese Patent Application No. 9-33506 filed on Feb. 18, 1997, including specification, claims, drawings, and summary are incorporated herein by reference in its entirety.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A surface inspection apparatus which comprises:

a laser element for emitting a laser light;

a deflecting scanning mirror having a polygonal periphery, each peripheral face of the periphery being a mirror face, the deflecting scanning mirror rotating about a center shaft thereof in a peripheral direction for reflecting the laser light emitted from the laser element during the rotation of the deflecting scanning mirror around the center shaft, wherein the laser light strikes the mirror face from a direction orthogonal to an axial direction of the center shaft;

two photodetectors for detecting a scattered reflected light at a surface of an object to be inspected when the laser light from the laser element and reflected by the deflecting scanning mirror scans the surface of the object, the photodetectors being arranged symmetrically with respect to an optical axis of the scanning light, wherein the surface of the object is inspected based on illumination positions at photodetecting faces of the photodetectors; and an optical element disposed between the deflecting scanning mirror and the object for moving an optical axis of the laser light reflected by the deflecting scanning mirror such that the illumination positions at the photodetecting faces of the respective photodetectors agree or nearly agree with each other, thus minimizing a surface inspection error.

2. A surface inspection apparatus according to claim 1, wherein the optical element has a reflection face for reflecting the laser light reflected by the deflecting scanning mirror and a reflection angle-changing member for changing a reflection angle of the laser light at the reflection face such that the optical axis of the laser light is moved.

3. A surface inspection apparatus according to claim 1, wherein the optical element is a strip-shaped plate-like body having at least one end part pressed and held by a retainer member to a pedestal, the retainer member being formed of a thin plate and being provided with a pressing part at one end thereof for pressing the optical element and a fixed part at the other end thereof fixed to the pedestal, wherein the retainer member extends in an axial direction of the optical element.

4. A surface inspection apparatus according to claim 2, wherein the optical element is a strip-shaped plate-like body having at least one end part pressed and held by a retainer member to a pedestal, the retainer member being formed of a thin plate and being provided with a pressing part at one end thereof for pressing the optical element and a fixed part at the other end thereof fixed to the pedestal, wherein the retainer member extends in an axial direction of the optical element.

5. A surface inspection apparatus according to claim 1, wherein the optical element is a prism of a wedge-shaped cross section.

6. A surface inspection method which comprises:

emitting a laser light to a deflecting scanning mirror having a polygonal periphery, each peripheral face of the periphery being a mirror face, the deflecting scanning mirror rotating about a center shaft thereof in a peripheral direction for reflecting the emitted laser light during the rotation of the deflecting scanning mirror around the center shaft, wherein the laser light strikes the mirror face from a direction orthogonal to an axial direction of the center shaft;

scanning a surface of an object to be inspected by a scanning light which is the laser light reflected at the mirror face;

detecting scattered reflected light reflected at the surface of the object, wherein the detecting is accomplished by two photodetectors arranged symmetrically with respect to an optical axis of the scanning light, thereby inspecting the surface of the object; and moving the optical axis of the scanning light to the surface of the object when the scanning light is projected so that illumination positions at photodetecting faces of the respective photodetectors agree or nearly agree with each other, to thereby minimize a surface inspection error.

* * * * *